United States Patent
Kanaya et al.

(10) Patent No.: US 8,568,779 B2
(45) Date of Patent: Oct. 29, 2013

(54) METHOD FOR PRODUCING COENZYME Q10 PARTICLE

(75) Inventors: Kento Kanaya, Takasago (JP); Shiro Kitamura, Takasago (JP); Takahiro Ueda, Takasago (JP)

(73) Assignee: Kaneka Corporation, Osaka-shi (JP)

(*) Notice: Subject to any disclaimer, the term of this patent is extended or adjusted under 35 U.S.C. 154(b) by 426 days.

(21) Appl. No.: 12/522,792

(22) PCT Filed: Jan. 10, 2008

(86) PCT No.: PCT/JP2008/050180
§ 371 (c)(1),
(2), (4) Date: Jul. 10, 2009

(87) PCT Pub. No.: WO2008/084828
PCT Pub. Date: Jul. 17, 2008

(65) Prior Publication Data
US 2010/0004473 A1 Jan. 7, 2010

(30) Foreign Application Priority Data

Jan. 11, 2007 (JP) ................................. 2007-003143
Jan. 11, 2007 (JP) ................................. 2007-003144

(51) Int. Cl.
*A61K 9/16* (2006.01)
*A61K 31/122* (2006.01)
*C07C 46/10* (2006.01)
*A61K 9/107* (2006.01)
*C07C 50/28* (2006.01)
*C09K 15/08* (2006.01)

(52) U.S. Cl.
CPC .............. *A61K 31/122* (2013.01); *A61K 9/16* (2013.01); *A61K 9/1075* (2013.01); *A23V 2250/314* (2013.01); *C07C 46/10* (2013.01); *C07C 50/28* (2013.01); *C09K 15/08* (2013.01)
USPC .......................................... 424/489; 552/307

(58) Field of Classification Search
None
See application file for complete search history.

(56) References Cited

U.S. PATENT DOCUMENTS

| 5,133,979 | A | * | 7/1992 | Clarke et al. ................ 426/49 |
| 5,688,742 | A | | 11/1997 | Mayeros, Jr. et al. |
| 6,346,276 | B1 | * | 2/2002 | Tanouchi et al. ............ 424/523 |
| 2002/0036154 | A1 | * | 3/2002 | Murari et al. ................ 206/538 |
| 2003/0104018 | A1 | * | 6/2003 | Bettle et al. ................. 424/401 |
| 2003/0228357 | A1 | | 12/2003 | Johnson et al. |
| 2004/0197886 | A1 | | 10/2004 | Ueda et al. |
| 2005/0074860 | A1 | | 4/2005 | Ueda et al. |
| 2005/0152865 | A1 | * | 7/2005 | Yamamoto et al. ........ 424/70.23 |
| 2006/0134085 | A1 | * | 6/2006 | Yamaguchi et al. ......... 424/94.1 |

FOREIGN PATENT DOCUMENTS

| JP | 56-103109 A | 8/1981 |
| JP | 09-124405 A | 5/1997 |
| JP | 2003-089669 A | 3/2003 |
| JP | 2004-123594 A | 4/2004 |
| JP | 2005-526020 A | 9/2005 |
| JP | 2006-213601 A | 8/2006 |
| WO | WO 03-006411 A1 | 1/2003 |
| WO | WO 2005-033054 A1 | 4/2005 |

OTHER PUBLICATIONS

F Carli, EE Chiellini, B Bellich, S Macchiavelli, G Cadelli. "Ubidecarenone nanoemulsified composite systems." International Journal of Pharmaceutics, vol. 291, 2005, pp. 113-118.*

* cited by examiner

*Primary Examiner* — Frederick Krass
*Assistant Examiner* — Isaac Shomer
(74) *Attorney, Agent, or Firm* — Leydig, Voit & Mayer, Ltd.

(57) ABSTRACT

The present invention aims to provide a production method capable of industrially and producing coenzyme $Q_{10}$ particles having a high content and superior powder flowability characteristics by simple facility and convenient operations. The present invention provides a method of producing coenzyme $Q_{10}$ particles, including mixing coenzyme $Q_{10}$ and a poor solvent by stirring at a temperature not less than the melting point of coenzyme $Q_{10}$, dispersing coenzyme $Q_{10}$ into the form of oil droplets, and cooling them to a solidification temperature of coenzyme $Q_{10}$ or below while stirring the dispersion to give solid particles, wherein the poor solvent is an aqueous solution comprising an organic solvent and/or a surfactant having an HLB of 6 or above. According to the production method of the present invention, coenzyme $Q_{10}$ particles markedly superior in powder characteristics, and having, for example, a powder flowability index of not less than 80 can be obtained.

17 Claims, 1 Drawing Sheet

METHOD FOR PRODUCING COENZYME Q10 PARTICLE

TECHNICAL FIELD

The present invention relates to a production method of coenzyme Q10 particles. Coenzyme $Q_{10}$ is a compound useful as a superior food, food with nutrient function claims, food for specified health uses, nutritional supplement, nutritional product, animal drug, beverage, feed, pet food, cosmetic, pharmaceutical, therapeutic drug, prophylactic drug or the like.

BACKGROUND ART

Coenzyme Q is an essential component widely distributed in living organisms from bacterium to mammal, and is known as a constituent component of an electron transport system of mitochondria in a living cell. Coenzyme Q includes an oxidized type and a reduced type. It repeats oxidization and reduction in mitochondria, thereby functioning as a transduction component in the electron transport system, and reduced coenzyme Q is known to have an antioxidant action. In human, coenzyme $Q_{10}$, which is a coenzyme Q having a side chain with 10 repeat units, is the main component, and generally, about 40-90% thereof is a reduced type in the living body. The physiological action of coenzyme $Q_{10}$ includes activation of energy production by mitochondria-activating action, activation of cardiac function, cellular membrane stabilization effect, cell protection effect by antioxidant action and the like.

Of the coenzyme $Q_{10}$, oxidized coenzyme $Q_{10}$ is used as a health food in Europe and the United States and as a drug for congestive heart failure in Japan. In recent years, it is also used as a food with nutrient function claims in Japan. Particularly, products of oxidized coenzyme $Q_{10}$ contained in a soft capsule have been mainly used in the fields of health food and food with nutrient function claims. On the other hand, reduced coenzyme $Q_{10}$ has not attracted much attention heretofore. In recent years, however, it has been reported to be more effective than oxidized coenzyme $Q_{10}$ in various applications. For example, a composition containing reduced coenzyme $Q_{10}$ has been reported to be superior to conventional oxidized coenzyme $Q_{10}$ alone in the oral absorbability (patent document 1).

The bulk powders of coenzyme $Q_{10}$, which may be reduced coenzyme $Q_{10}$, oxidized coenzyme $Q_{10}$ or a mixture of them, can be obtained, for example, by producing a crude purification product of coenzyme $Q_{10}$ by a method such as synthesis, fermentation, extraction from naturally occurring substances and the like, concentrating a coenzyme $Q_{10}$ fraction in an outflow fluid by chromatography, and crystallizing the concentrate by crystal precipitation. However, the thus-obtained bulk powder of coenzyme $Q_{10}$ takes the form of an ultrafine plate crystal or capillary crystal, which may be stirred up as dust during handling of the powder or stick to a solid surface, causing difficulty in brushing off the entire amount of the powder from a packaging material such as a bag and the like since it attaches thereto. In addition, the powder often agglomerates to form a mass during preservation, thus rendering the handling very difficult, and is known to show markedly poor powder flowability characteristics. Moreover, the powder attaches to bulk powder containers and formulation apparatuses during tableting or capsule filling, thus causing problems in productivity and operability since coenzyme $Q_{10}$ preparations cannot be formulated smoothly, and the like. Therefore, the development of a granulation or particulate technique capable of improving the powder property of a bulk powder of coenzyme $Q_{10}$ has been desired. As a granulation or particulate method of oxidized coenzyme $Q_{10}$, for example, spray-coating of a coating substance while mixing an excipient with oxidized coenzyme $Q_{10}$ in a fluidized bed apparatus and the like is known (patent document 2).

However, such granulation method has problems in that the content of coenzyme $Q_{10}$ in the obtained particles unavoidably decreases due to the use of large amounts of an excipient and a coating agent, a special facility is necessary and the like. Even when such granulation method is used, moreover, since the powder flowability characteristics are not sufficient, the powder or particles of the obtained coenzyme $Q_{10}$ may be ultrafine or a large solid. Thus, the powder and particles are not handled sufficiently easily, and are not satisfactory for application to various uses such as formulation of preparations and the like.

In addition, a granulation method that affords agglomerates of a high content of oxidized coenzyme $Q_{10}$ crystals by crystallization of oxidized coenzyme $Q_{10}$ in a system concurrently containing an auxiliary solvent having affinity for oxidized coenzyme $Q_{10}$ is known (patent document 3). Moreover, a method of improving the flowability during formulation of a preparation of oxidized coenzyme $Q_{10}$ is also reported (patent document 4).

On the other hand, as a granulation method for reduced coenzyme $Q_{10}$, a method including crystallizing an oily substance of reduced coenzyme $Q_{10}$ in water to give reduced coenzyme $Q_{10}$ (patent document 5) and a method including adding a liquid phase of high concentration of reduced coenzyme $Q_{10}$ to a poor solvent for granulation (patent document 6) are known. According to these granulation methods, control of the resulting particle size is difficult, and an additional facility such as a tank for preparation of a high concentration liquid phase, a pump for delivery of liquid and the like is necessary.

Among the reports of solidification granulation methods of general liposoluble substances is an embodiment wherein a low melting point substance is melted in water at a temperature not lower than the melting point to give droplets, which are cool-solidified to give granules (patent document 7).

patent document 1: JP-A-10-109933
patent document 2: JP-A-2006-213601
patent document 3: JP-A-2004-130201
patent document 4: JP-A-2004-123594
patent document 5: WO 03/006411
patent document 6: JP-A-2003-89669
patent document 7: JP-A-9-124405

DISCLOSURE OF THE INVENTION

Problems to be Solved by the Invention

The problem of the present invention is to provide a production method capable of efficient industrial production of coenzyme $Q_{10}$ particles having a high content and superior powder flowability characteristics, by simple facility and convenient operations.

Means of Solving the Problems

The present inventors have conducted intensive studies in an attempt to solve the aforementioned problem and found that coenzyme $Q_{10}$ particles having a high content and superior powder flowability characteristics can be produced efficiently by an industrially possible method by stirring and dispersing coenzyme $Q_{10}$ into the form of oil droplets in a particular solvent and solidifying them by cooling with stirring, which resulted in the completion of the present invention. Accordingly, the present invention provides the following.

[1] A method of producing coenzyme $Q_{10}$ particles, comprising mixing coenzyme $Q_{10}$ and a poor solvent by stirring at a temperature not less than the melting point of coenzyme $Q_{10}$, dispersing coenzyme $Q_{10}$ into the form of oil droplets, and cooling them to a solidification temperature of coenzyme $Q_{10}$ or below while stirring the dispersion to give solid particles, wherein the poor solvent is an aqueous solution comprising an organic solvent and/or a surfactant having HLB of 6 or above.

[2] The production method of [1], wherein the poor solvent is an aqueous solution comprising at least one kind of an organic solvent selected from the group consisting of ketones, alcohols, nitriles and ethers.

[3] The production method of [2], wherein the organic solvent is an alcohol having a carbon number of 1 to 5.

[4] The production method of [2], wherein the poor solvent is an aqueous solution containing ethanol at a concentration of 10-70% by volume.

[5] The production method of [1], wherein the surfactant is at least one selected from the group consisting of partial glyceride of fatty acid, phospholipid, saponin, sucrose fatty acid ester, sorbitan fatty acid ester, sorbitan polyoxyethylene fatty acid ester, polyglycerin fatty acid ester and condensed ricinoleic acid polyglyceride.

[6] The production method of [1], wherein the surfactant is at least one selected from the group consisting of partial glyceride of fatty acid, sucrose fatty acid ester, sorbitan polyoxyethylene fatty acid ester and polyglycerin fatty acid ester.

[7] The production method of [1], [5] or [6], wherein the concentration of the surfactant in the poor solvent is not less than 0.001 wt %.

[8] The production method of any of [1] to [7], wherein the poor solvent further comprises a water-soluble dispersing agent.

[9] The production method of [8], wherein the water-soluble dispersing agent is at least one kind selected from the group consisting of gum arabic, gelatin, agar, starch, pectin, carageenan, casein, alginic acids, soybean polysaccharides, pullulan, celluloses, xanthan gum, polyvinyl alcohol and a surfactant having HLB of less than 6.

[10] The production method of [8] or [9], wherein the concentration of the water-soluble dispersing agent in the poor solvent is 0.001-5 wt %.

[11] The production method of any of [1] to [10], wherein the dispersion of coenzyme $Q_{10}$ concurrently comprises fats and oils, waxes, fatty acids or fatty acid ester derivatives.

[12] The production method of any of [1] to [11], wherein the stirring is performed under the conditions of required power for stirring per unit volume of not less than 0.01 kW/m$^3$.

[13] The production method of any of [1] to [12], wherein the dispersion of coenzyme $Q_{10}$ is cooled at a cooling rate of 0.01-1.2° C./min.

[14] The production method of any of [1] to [13], wherein the coenzyme $Q_{10}$ comprises reduced coenzyme $Q_{10}$.

[15] A coenzyme $Q_{10}$ particle having a Dr. CARR's Flowability Index of not less than 80.

[16] The coenzyme $Q_{10}$ particle of [15], having an angle of repose of 20-45°.

[17] The coenzyme $Q_{10}$ particle of [15] or [16], having a sphericity of not less than 0.7.

[18] The coenzyme $Q_{10}$ particle of any of [15] to [17], which is a spherical or granular particle having a mean particle size of 50-1000 μm.

[19] The coenzyme $Q_{10}$ particle of any of [15] to [18], which has a coenzyme $Q_{10}$ content of not less than 90 wt %.

[20] The coenzyme $Q_{10}$ particle of any of [15] to [19], having crystallinity of not more than 90%.

[21] The coenzyme $Q_{10}$ particle of any of [15] to [20], wherein coenzyme $Q_{10}$ comprises reduced coenzyme $Q_{10}$.

Effect of the Invention

The particles of coenzyme $Q_{10}$ obtained by the present invention are not stirred up as dust during handling, are easily brushed off from a packaging material such as a bag and the like, are easily blended with other substances, have a uniform particle size and are superior in powder flowability characteristics, do not easily attach to bulk powder containers and preparation apparatuses, and are superior in apparatus filling property. In addition, the production method of the present invention can be performed using simple facility and by convenient operations, enables granulation even without using a dispersing agent, an excipient and the like, and enables production of particles having a high coenzyme $Q_{10}$ content.

According to the present invention, coenzyme $Q_{10}$ particles having a high content and superior in powder property can be efficiently produced in large amounts at a low production cost.

BEST MODE FOR CARRYING OUT THE INVENTION

The embodiment of the present invention is explained in detail in the following.

The production method of the present invention produces coenzyme $Q_{10}$ particles by mixing coenzyme $Q_{10}$ and a poor solvent by stirring at a temperature not less than the melting point of coenzyme $Q_{10}$, dispersing coenzyme $Q_{10}$ into the form of oil droplets, and cooling them to a solidification temperature of coenzyme $Q_{10}$ or below while stirring the dispersion, and the method is characterized by the use of a particular poor solvent to produce a coenzyme $Q_{10}$ oil droplet dispersion.

Coenzyme $Q_{10}$ is an essential component widely distributed in living organisms and, as mentioned above, includes oxidized type and reduced type. In the present invention, any of the oxidized coenzyme $Q_{10}$ and reduced coenzyme $Q_{10}$ can be used as the coenzyme $Q_{10}$ to obtain particles superior in powder flowability characteristics. Needless to say, coenzyme $Q_{10}$ may be a mixture of oxidized coenzyme $Q_{10}$ and reduced coenzyme $Q_{10}$. The production method of the present invention can be applied to any of the forms mentioned above. However, since reduced coenzyme $Q_{10}$ is superior to oxidized coenzyme $Q_{10}$ in the oral absorbability and other pharmacological effects, and more effective when applied to coenzyme $Q_{10}$ containing reduced coenzyme $Q_{10}$ inferior in powder property, the method is generally preferably applied as coenzyme $Q_{10}$ to reduced coenzyme $Q_{10}$ or a mixture of oxidized coenzyme $Q_{10}$ and reduced coenzyme $Q_{10}$.

While the mixing ratio when coenzyme $Q_{10}$ is a mixture of the oxidized type and the reduced type is not particularly limited, the ratio of reduced coenzyme $Q_{10}$ in coenzyme $Q_{10}$ is preferably not less than 20 wt %, more preferably not less than 40 wt %, more preferably not less than 50 wt %, most preferably not less than 60 wt %, particularly preferably not less than 80 wt %, specially not less than about 90 wt %, essentially not less than about 96 wt %. While the upper limit of the content of the reduced coenzyme $Q_{10}$ is not particularly limited, it is generally not more than about 99.9 wt % in the case of a mixture. Needless to say, reduced coenzyme $Q_{10}$ can be used alone.

In the present specification, an indication of coenzyme $Q_{10}$ alone does not question whether it is oxidized type or reduced type. When the two are mixed, the term also refers to the mixture as a whole.

Coenzyme $Q_{10}$ to be used for the production method of the present invention may be commercially available or produced and purified by a known production method. When reduced coenzyme $Q_{10}$ or a mixture of oxidized coenzyme $Q_{10}$ and reduced coenzyme $Q_{10}$ is used as coenzyme $Q_{10}$, reduced coenzyme $Q_{10}$ may be obtained by reducing an oily substance of oxidized coenzyme $Q_{10}$ in water. In this case, examples of the usable reducing agent include metal hydride compound, iron (metal or iron as salt), zinc (zinc as metal), hydrosulfurous acids, ascorbic acids and the like.

While the above-mentioned metal hydride compound is not particularly limited, examples thereof include sodium borohydride, lithium aluminum hydride and the like. The amount of the above-mentioned metal hydride compound to be used varies depending on the kind of the metal hydride compound and cannot be uniformly defined. However, it is generally preferably theoretical hydrogen equivalent—3-fold amount thereof.

Reduction using the above-mentioned iron or zinc is normally performed using an acid. While the acid to be used is not particularly limited, it is, for example, fatty acid such as acetic acid and the like, sulfonic acid such as methanesulfonic acid and the like, inorganic acid such as hydrochloric acid, sulfuric acid and the like, and the like. It is preferably an inorganic acid, more preferably sulfuric acid. While the amount of iron to be used is not particularly limited, for example, the reduction can be performed using preferably not less than about 1/5 weight relative to the charge weight of oxidized coenzyme $Q_{10}$. While the upper limit is not particularly limited, it is not more than about 2-fold weight from the economic aspect and the like. Iron can be used not only in the form of metal iron but also salt such as iron(II) sulfate and the like. While the amount of zinc to be used is not particularly limited, the reduction can be preferably performed using not less than about 1/10 weight relative to the charge weight of oxidized coenzyme $Q_{10}$. While the upper limit is not particularly limited, it is not more than about 2-fold weight from the economic aspect and the like.

The above-mentioned hydrosulfurous acids are not particularly limited, hydrosulfite is generally used. The hydrosulfite is not particularly limited, alkali metal salt, alkaline earth metal salt, ammonium salt and the like are preferable, alkali metal salts such as lithium salt, sodium salt, potassium salt and the like are more preferable, and sodium salt is most preferable.

While the amount of the above-mentioned hydrosulfurous acids to be used is not particularly limited, it is normally not less than about 1/3 weight, preferably not less than about 2/3 weight, more preferably not less than about 3/5 weight, relative to the charge weight of oxidized coenzyme $Q_{10}$. A large amount thereof does not cause particular inconvenience but, from the economical aspects, not more than about twice the weight, preferably not more than equivalent weight, is generally employed. Therefore, the reduction can be preferably performed using about 2/3 weight—about equivalent weight thereof.

The reduction using the above-mentioned hydrosulfurous acids is performed generally pH 7 or below, preferably pH 3-7, more preferably pH 3-6, from the aspects of yield and the like. The above-mentioned pH can be adjusted using an acid (e.g., inorganic acid such as hydrochloric acid, sulfuric acid and the like) or a base (e.g., alkali metal hydroxide such as sodium hydroxide and the like).

The above-mentioned ascorbic acids are not particularly limited. Examples thereof include not only ascorbic acid but also those analogous to ascorbic acid such as rhamno-ascorbic acid, arabo-ascorbic acid, gluco-ascorbic acid, fuco-ascorbic acid, glucohepto-ascorbic acid, xylo-ascorbic acid, galacto-ascorbic acid, gulo-ascorbic acid, allo-ascorbic acid, erythro-ascorbic acid, 6-deoxyascorbic acid and the like. In addition, an ester or salt thereof can also be used. They may also be L form, D form or racemate. Specific examples include L-ascorbic acid, L-ascorbic acid palmitate, L-ascorbic stearate, L-sodium ascorbate, L-calcium ascorbate, D-arabo-ascorbic acid and the like. While any of the above-mentioned ascorbic acids can be preferably used, in consideration of easy separation from the resulting reduced coenzyme $Q_{10}$ and the like, water-soluble ones from among the above-mentioned ascorbic acids are particularly preferably used. Most preferred from the aspects of easy availability, cost and the like are L-ascorbic acid, D-arabo-ascorbic acid, L-sodium ascorbate and the like.

The amount of the above-mentioned ascorbic acids to be used is not particularly limited, and only needs to be an effective amount capable of converting oxidized coenzyme $Q_{10}$ to reduced coenzyme $Q_{10}$. Generally, it is normally not less than is 1-fold molar amount, preferably not less than 1.2-fold molar amount, relative to oxidized coenzyme $Q_{10}$. While the upper limit is not particularly limited, in consideration of the economic aspect, it is normally 10-fold molar amount, preferably 5-fold molar amount, more preferably 3-fold molar amount.

From among the above-mentioned reducing agents, particularly, zinc, hydrosulfurous acids and ascorbic acids are preferable, hydrosulfurous acids (specifically hydrosulfite) and ascorbic acids are particularly more preferable, and ascorbic acids are particularly preferable, from the aspects of reducing ability, yield and quality.

In the production method of the present invention, after the above-mentioned reduction reaction, the resulting oily substance containing reduced coenzyme $Q_{10}$ is used as it is and dispersed and solidified in a poor solvent to give particles. Where necessary, an oily substance of reduced coenzyme $Q_{10}$ can also be collected by partitioning, extraction and the like, repeatedly washed with, for example, water, brine etc. to remove contaminants, and put to use.

As mentioned above, the poor solvent to be used in the present invention needs to disperse coenzyme $Q_{10}$ into the form of oil droplets at not less than the melting point thereof, and maintain its dispersion state well. As such poor solvent, an aqueous solution containing an organic solvent and/or a surfactant having an HLB of not less than 6 is used in the present invention. Here, one capable of completely dissolving coenzyme $Q_{10}$ at not less than the melting point thereof, namely, a good solvent, cannot afford a coenzyme $Q_{10}$ dispersion and does not fall under a poor solvent in the present invention.

In the production method of the present invention, the organic solvent that can be contained in an aqueous solution to be used as a poor solvent is not particularly limited. However, a water-soluble organic solvent is preferable. Among such solvents, at least one kind of organic solvent from ketones, alcohols, nitrites and ethers is more preferable.

While the above-mentioned ketones are not particularly limited, normally, one having a carbon number of 3-6 is preferably used. Specific examples include acetone, methylethyl ketone, methylbutylketone, methylisobutylketone and the like. Among these, acetone, methylethyl ketone and the like are preferable, and acetone is most preferable.

The above-mentioned alcohols may be cyclic or acyclic, and saturated or unsaturated, and are not particularly limited. Generally, saturated one is preferably used. Particularly, monovalent alcohol having a carbon number of 1-5, divalent alcohol having a carbon number of 2-5 and trivalent alcohol having a carbon number of 3 are preferable.

Specific examples of monohydric alcohol include methanol, ethanol, 1-propanol, 2-propanol, 1-butanol, 2-butanol, isobutyl alcohol, 1-pentanol, 2-pentanol, 3-pentanol and the like. Examples of divalent alcohol include 1,2-ethanediol, 1,2-propanediol, 1,3-propanediol, 1,2-butanediol, 1,3-butanediol, 1,4-butanediol, 2,3-butanediol, 1,5-pentanediol and the like. As the trivalent alcohol, glycerol and the like can be used.

The above-mentioned nitriles may be cyclic or acyclic, and saturated or unsaturated, and are not particularly limited. Generally, saturated one is preferably used. Normally, one having a carbon number of 2-8, particularly 2-6, especially 2-4, is preferably used. Specific examples thereof include acetonitrile, propionitrile, succinonitrile, butyronitrile, isobutyronitrile and the like.

The above-mentioned ethers may be cyclic or acyclic, and saturated or unsaturated, and are not particularly limited. Generally, saturated one is preferably used. Specific examples thereof include diethyl ether, methyl tert-butylether, anisole, dioxane, tetrahydrofuran and the like.

In the present invention, alcohol is preferably used from among the above-mentioned organic solvents. More preferably, alcohol having a carbon number of 1 to 5 is used, and most preferably, ethanol is used.

In the production method of the present invention, when an aqueous solution containing an organic solvent is used as a poor solvent, the concentration of the organic solvent in the poor solvent is not particularly limited, and can be appropriately selected from the range of generally 1-99 v/v % according to the dispersion state of coenzyme $Q_{10}$ oil droplets.

For example, when ethanol is used as the organic solvent, the concentration thereof in a poor solvent is not particularly limited. It is preferably 10-70 v/v %, more preferably 10-50 v/v %. In particular, when oxidized coenzyme $Q_{10}$ or coenzyme $Q_{10}$ having a high oxidized coenzyme $Q_{10}$ ratio is used, the concentration is more preferably 30-50 v/v %.

Oxidized coenzyme $Q_{10}$ and reduced coenzyme $Q_{10}$ show somewhat different compatibility with ethanol. In the case of reduced coenzyme $Q_{10}$, a good oil droplet dispersion can be obtained even when an aqueous solution having a low ethanol content is used, as compared to oxidized coenzyme $Q_{10}$. From such aspect, when oxidized coenzyme $Q_{10}$ alone, or coenzyme $Q_{10}$ having a high oxidized coenzyme $Q_{10}$ ratio is used as coenzyme $Q_{10}$ in the production method of the present invention, 30-50 v/v % aqueous ethanol solution (aqueous solution containing ethanol at the concentration) is optimally used as a poor solvent. When reduced coenzyme $Q_{10}$ alone, or coenzyme $Q_{10}$ having a high reduced coenzyme $Q_{10}$ ratio is used as coenzyme $Q_{10}$ in the production method of the present invention, 10-50 v/v % aqueous ethanol solution (aqueous solution containing ethanol at the concentration) is optimally used as a poor solvent.

In the granulation method of the present invention, when an aqueous ethanol solution having a concentration of less than 10 v/v % is used as a poor solvent, a rapid agglomeration phenomenon occurs between oil droplets, promoting production of agglomerated mass during solidification of melt-dispersed coenzyme $Q_{10}$ oil droplets. Consequently, coenzyme $Q_{10}$ particles more uniform and superior in powder flowability characteristics are sometimes difficult to obtain. Moreover, when an aqueous ethanol solution having a concentration exceeding 70 v/v % is used as a poor solvent, the compatibility between the poor solvent and coenzyme $Q_{10}$ oil droplets increases, due to which the organic solvent is absorbed by the coenzyme $Q_{10}$ particles to cause disintegration of particle shape and high concentration of residual organic solvent. Consequently, coenzyme $Q_{10}$ particles having better quality are sometimes difficult to obtain.

In the production method of the present invention, as the surfactant that can be contained in an aqueous solution to be used as a poor solvent, any can be used as long as it has an HLB of not less than 6. One usable for food or pharmaceutical products is preferable. Examples thereof include partial glyceride of fatty acid, phospholipid, saponin, sucrose fatty acid ester, sorbitan fatty acid ester, sorbitan polyoxyethylene fatty acid ester, polyglycerin fatty acid ester, condensed ricinoleic acid polyglyceride and the like, which have an HLB of not less than 6. Among these, partial glyceride of fatty acid, sucrose fatty acid ester, sorbitan polyoxyethylene fatty acid ester and polyglycerin fatty acid ester are more preferable.

Examples of the above-mentioned partial glyceride of fatty acid include monoglycerol fatty acid esters such as monoglycerol monocaprylate, monoglycerol monocaprate, monoglycerol dicaprylate, monoglycerol dicaprate, monoglycerol dilaurate, monoglycerol dimyristate, monoglycerol distearate, monoglycerol dioleate, monoglycerol dierucate, monoglycerol dibehenate and the like, fatty acid and organic acid esters of monoglycerol such as caprylic acid and succinic acid ester of monoglycerol, stearic acid and citric acid ester of monoglycerol, stearic acid and acetic acid ester of monoglycerol, stearic acid and succinic acid ester of monoglycerol, stearic acid and lactic acid ester of monoglycerol, stearic acid and diacetyltartaric acid ester of monoglycerol, oleic acid and citric acid ester of monoglycerol and the like, and the like.

Examples of the above-mentioned phospholipid include soybean lecithin, egg-yolk lecithin, enzyme decomposition phospholipids thereof and the like.

Examples of the above-mentioned saponins include sophora saponin, quillaja saponin, soybean saponin, yucca saponin and the like.

Examples of the above-mentioned sucrose fatty acid ester include sucrose wherein one or more of the hydroxyl groups are esterified with fatty acid each having a carbon number of 6-22, such as sucrose laurate, sucrose myristate, sucrose palmitate, sucrose stearate, sucrose oleate, sucrose erucate, sucrose behenate, and the like.

Examples of the above-mentioned sorbitan fatty acid ester include sorbitan wherein one or more of the hydroxyl groups are esterified with fatty acid each having a carbon number of 6-18, such as sorbitan monolaurate, sorbitan monopalmitate, sorbitan monooleate, sorbitan monostearate and the like.

Examples of the above-mentioned sorbitan polyoxyethylene fatty acid ester include sorbitan polyoxyethylene monopalmitate, sorbitan polyoxyethylene monostearate, sorbitan polyoxyethylene monooleate, sorbitan polyoxyethylene tristearate, sorbitan polyoxyethylene trioleate and the like.

Examples of the above-mentioned polyglycerin fatty acid ester include polyglycerol containing polyglycerol having a degree of polymerization of 2 to 10 as a main component, and polyglycerol wherein one or more of the hydroxyl groups are esterified with fatty acid each having a carbon number of 6-22. Specifically, for example, hexaglycerol monocaprylate, hexaglycerol dicaprylate, decaglycerol monocaprylate, triglycerol monolaurate, tetraglycerol monolaurate, pentaglycerol monolaurate, hexaglycero monolaurate, decaglycerol monolaurate, triglycerol monomyristate, pentaglycerol monomyristate, pentaglycerol trimyristate, hexaglycerol monomyristate, decaglycerol monomyristate, diglycerol monooleate, triglycerol monooleate, tetraglycerol monooleate, pentaglycerol monooleate, hexaglycerol monooleate, decaglycerol monooleate, diglycerol monostearate, triglycerol monostearate, tetraglycerol monostearate, pentaglycerol monostearate, pentaglycerol tristearate, hexaglycerol monostearate, hexaglycerol tristearate, hexaglycerol distearate, decaglycerol monostearate, decaglycerol distearate, decaglycerol tristearate and the like can be mentioned.

Examples of the above-mentioned condensed ricinoleic acid polyglyceride include one containing polyglycerol having an average degree of polymerization of 2-10, and one containing polyricinoleic acid having an average condensation degree (average number of condensed ricinoleic acid) of 2-4. For example, tetraglycerol condensed ricinoleic acid ester, pentaglycerol condensed ricinoleic acid ester, hexaglycerol condensed ricinoleic acid ester and the like can be mentioned.

Needless to say, the surfactants shown here can also be used in a combination of two or more kinds thereof.

These surfactants having an HLB of not less than 6 can be used. From the aspects of easy particulation, however, the HLB is more preferably not less than 8, still more preferably not less than 10, particularly not less than 12.

When the above-mentioned surfactants are used in the present invention, the concentration of the surfactant in a poor solvent is not particularly limited. In consideration of easy particle formation, it is generally not less than about 0.001 wt %, preferably not less than about 0.005 wt %, more preferably not less than about 0.01 wt %. When the concentration of the surfactant in a poor solvent is high, the upper limit thereof is normally not more than about 5 wt %, preferably not more than about 1 wt %, more preferably not more than about 0.5 wt %, more preferably not more than about 0.1 wt %, from the economical aspect as well as the possibility of the obtained coenzyme $Q_{10}$ particles becoming too ultrafine.

The poor solvent to be used in the production method of the present invention only needs to be an aqueous solution containing either or both of an organic solvent or a surfactant having an HLB of not less than 6. To obtain coenzyme $Q_{10}$ particles more superior in the powder characteristics, use of an aqueous solution containing at least an organic solvent, namely, an aqueous solution containing at least an organic solvent alone, or both an organic solvent and a surfactant having an HLB of not less than 6 as a poor solvent is more preferable.

When an aqueous solution containing both an organic solvent and a surfactant having an HLB of not less than 6 is used as a poor solvent, a preferable kind and amount of use thereof may be any of the above-mentioned examples. It is preferable to preferentially employ specific preferable examples and preferable amount of use of the organic solvent.

In the production method of the present invention, a poor solvent may further contain a slight amount of a water-soluble dispersing agent. While the water-soluble dispersing agent that can be used in the production method of the present invention is not particularly limited, gum arabic, gelatin, agar, starches, pectin, carageenan, casein, alginic acids, soybean polysaccharides, pullulan, curdlan, celluloses, xanthan gum, polyvinyl alcohol, as well as surfactants having an HLB of less than 6 and the like can be used. By adding such a water-soluble dispersing agent to a poor solvent in which coenzyme $Q_{10}$ is dispersed, ultrafine and highly uniform and highly spherical coenzyme $Q_{10}$ particles can be obtained while maintaining a high content of coenzyme $Q_{10}$ in the obtained particles.

Examples of the above-mentioned starches include water-soluble starch, cyclodextrin, cluster dextrin, indigestible dextrin and the like.

Examples of the above-mentioned alginic acids include alginic acid, sodium alginate, potassium alginate and the like.

The above-mentioned soybean polysaccharides are polysaccharides extracted from soybean, which are water-soluble dietary fibers.

Examples of the above-mentioned celluloses include crystalline cellulose, hydroxymethylcellulose, hydroxyethylcellulose, hydroxyethylmethylcellulose, carboxymethylcellulose, hydroxypropylmethylcellulose, hydroxypropylcellulose, ethylcellulose, methylcellulose and the like.

Examples of the above-mentioned surfactant having an HLB of less than 6 include glycerol fatty acid esters (e.g., monoglycerol fatty acid organic acid ester, polyglycerin fatty acid ester etc.: specifically, stearic acid and citric acid ester of monoglycerol, stearic acid and acetic acid ester of monoglycerol, stearic acid and succinic acid ester of monoglycerol, caprylic acid and succinic acid ester of monoglycerol, stearic acid and lactic acid ester of monoglycerol, stearic acid and diacetyltartaric acid ester of monoglycerol, triglycerol monolaurate, triglycerol monomyristate, triglycerol monooleate, triglycerol monostearate, pentaglycerol monomyristate, pentaglycerol trimyristate, pentaglycerol monooleate, pentaglycerol trioleate, pentaglycerol monostearate, pentaglycerol stearate, pentaglycerol monostearate, hexaglycerol monocaprylate, hexaglycerol dicaprylate, hexaglycerol monolaurate, hexaglycerol monomyristate, hexaglycerol monooleate, hexaglycerol monostearate, decaglycerol monolaurate, decaglycerol monomyristate, decaglycerol monooleate, decaglycerol monopalmitate, decaglycerol monostearate, decaglycerol distearate etc.), sucrose fatty acid esters (specifically, sucrose palmitate, sucrose stearate etc.), sorbitan fatty acid esters (specifically, sorbitan monostearate, sorbitan monooleate etc.), lecithins (e.g., egg-yolk lecithin, purified soybean lecithin, phosphatidylcholine, phosphatidylethanolamine, phosphatidylserine, sphingomyelin, dicetyl phosphoric acid, stearylamine, phosphatidylglycerol, phosphatidic acid, phosphatidylinositolamine, cardiolipin, ceramide phosphoryl ethanolamine, ceramide phosphoryl glycerol, lysolecithin etc.), which have an HLB of less than 6, and a mixture thereof and the like.

While the concentration of the water-soluble dispersing agent contained in a poor solvent is not particularly limited, the dispersing agent is preferably contained such that the concentration becomes 0.001-5 wt %, more preferably 0.01-1 wt %.

While the charge concentration of coenzyme $Q_{10}$ in a poor solvent in the production method of in the present invention is not particularly limited, a higher charge concentration of coenzyme $Q_{10}$ in a poor solvent is preferable from the aspect of productivity. For example, it is preferably not less than 10 g/L, particularly not less than 50 g/L. On the other hand, when the charge concentration of coenzyme $Q_{10}$ in a poor solvent is not less than 200 g/L, control of particle size becomes difficult and particles having high uniformity and high sphericity cannot be obtained easily. Thus, the charge concentration is preferably not more than the indicated level.

In the production method of the present invention, moreover, when coenzyme $Q_{10}$ is dispersed in a poor solvent, an oil component such as fats and oils, waxes, fatty acids, fatty acid ester derivatives and the like may also be concurrently contained to meet various objects. When articulation is performed in the co-presence of such oil component, the oil component can be contained in the obtained coenzyme $Q_{10}$ solid particles, and the temperature at which coenzyme $Q_{10}$ particles are dissolved, state of particle surface and the like can be conveniently changed variously.

While the above-mentioned fats and oils are not particularly limited, for example, natural fats and oils from animals and plants, synthetic fats and oils and processed fats and oils may be used. More preferably, one acceptable for use for foods, cosmetics or pharmaceutical products can be used. Examples of plant fats and oils include coconut oil, palm oil, palm kernel oil, linseed oil, camellia oil, brown rice germ oil, rapeseed oil, rice oil, peanut oil, corn oil, wheat germ oil, soybean oil, perilla oil, cottonseed oil, sunflower seed oil, kapok oil, evening primrose oil, shea butter, sal butter, cacao butter, sesame oil, safflower oil, olive oil, jojoba oil, tea oil, Japanese nutmeg oil, avocado oil, pumpkin seed oil, walnut oil, grapeseed oil and the like; examples of animal fats and oils include lard, milk fat, fish oil, beef tallow, egg-yolk oil and the like; furthermore, fats and oils processed therefrom by fractionation, hydrogenation or transesterification (e.g., hydrogenated oil). Of course, medium-chain fatty acid triglyceride (MCT) can also be used. A mixture thereof may be used.

Examples of the medium-chain fatty acid triglyceride include triglyceride wherein fatty acid has 6 to 12 carbon atoms, preferably 8 to 12 carbon atoms.

Among the above-mentioned fats and oils, oil from plant or animal, synthetic fats and oils, processed fats and oils and the like are preferable from the aspects of easy handling property, odor and the like. More preferable specific examples include coconut oil, palm oil, palm kernel oil, canola oil, rice oil, soy bean oil, cottonseed oil, safflower oil, olive oil, MCT and the like.

Examples of the above-mentioned waxes include, but are not limited to, waxes such as beeswax, rhus succedanea fruit wax, candelilla wax, rice bran wax, carnauba wax, snow wax, cotton wax, bayberry wax, ibota wax, whale wax, montan wax, rice bran wax, lanolin, kapok wax, sugarcane wax, jojoba wax, shellac wax and the like.

Examples of the above-mentioned fatty acids and ester derivatives thereof include, but are not limited to, caprylic acid, capric acid, lauric acid, myristic acid, palmitic acid, stearic acid, oleic acid, behenic acid, linoleic acid, linolenic acid and esters thereof, for example, methyl esters thereof, ethyl esters thereof and the like.

While the amount of such oil component to be added cannot be unconditionally defined and varies depending on the object, it is normally not more than about 60 wt %, preferably not more than about 40 wt %, more preferably not more than about 20 wt %, more preferably not more than about 10 wt %, of coenzyme $Q_{10}$.

In the production method of the present invention, moreover, an active substance other than coenzyme $Q_{10}$ can also be co-present, like the above-mentioned oil component.

While the above-mentioned active substance other than coenzyme $Q_{10}$ is not particularly limited, one acceptable for use for foods, cosmetics or pharmaceutical products is preferable. For example, glutathione, L-cysteine, N-acetylcysteine, α-lipoic acid, reduced α-lipoic acid, tocotrienol, vitamin E (α-tocopherol) and an ester derivative thereof, vitamin C (ascorbic acid) and an ester derivative or salt thereof, erythorbic acid and an ester derivative or salt thereof, vitamin A and an ester derivative thereof, carotenoid, rutin, zeaxanthine, astaxanthin, lycopene, flavonoid, L-carnitine and pharmacologically acceptable salts such as tartrate thereof, fumarate thereof and the like, acetyl-L-carnitine, propionyl-L-carnitine, magnesium, zinc, selenium, manganese, riboflavin, niacinamide, curcuminoid, proanthocyanidin, NADH (reduced nicotinamideadenine dinucleotide), NADPH (reduced nicotinamideadenine dinucleotide phosphoric acid), resveratrol, a bilberry extract, blessed thistle extract, licorice hydrophobic extract, highly unsaturated fatty acid of DHA, EPA and the like, and the like can be mentioned. The above-mentioned active ingredient is preferably lipophilic since it can be economically contained in the obtained coenzyme $Q_{10}$ particles. Particularly, tocotrienol, vitamin E (α-tocopherol) and an ester derivative thereof, ester derivative of vitamin C, ester derivative of erythorbic acid, vitamin A and an ester derivative thereof, carotenoid, rutin, astaxanthin, lycopene, flavonoid, curcuminoid, licorice hydrophobic extract and the like, particularly preferably, carotenoid, astaxanthin, vitamin E and an ester derivative thereof, ester derivative of vitamin C, licorice hydrophobic extract and the like are preferable. Needless to say, various components recited here can also be used in a mixture of two or more kinds thereof.

While the amount of the active substance other than coenzyme $Q_{10}$ to be added cannot be unconditionally defined and varies depending on the object, it is normally not more than about 50 wt %, preferably not more than about 30 wt %, more preferably not more than about 10 wt %, of coenzyme $Q_{10}$.

In the production method of the present invention, coenzyme $Q_{10}$ first needs to be dispersed as an oily substance in a poor solvent. In this case, the method of charging coenzyme $Q_{10}$ and poor solvent is not particularly limited. For example, when an aqueous solution containing an organic solvent is used as a poor solvent, a method wherein an organic solvent and water are charged at once, coenzyme $Q_{10}$ is added and melted to disperse oil droplets, a method wherein coenzyme $Q_{10}$ is added to a system using water alone as a solvent and melted to give oil droplets, an organic solvent is added dropwise thereto and the like to gradually allow addition by feeding and the like can be employed. It is preferable to charge an organic solvent and water and coenzyme $Q_{10}$ are charged at once, stirred and heated to melt coenzyme $Q_{10}$ into oil droplets. When an aqueous solution containing a surfactant is used as a poor solvent, the surfactant may be added to and mixed with coenzyme $Q_{10}$ in advance and then mixed with water. Alternatively, it may be added to and dissolved in water and then mixed with coenzyme $Q_{10}$, or it may be added after dispersing coenzyme $Q_{10}$ as an oily substance in water or added during dispersion. Of course, coenzyme $Q_{10}$ and water and a surfactant may be charged at once and the mixture may be heated and mixed.

The pH of the poor solvent in which coenzyme $Q_{10}$ oily substance is dispersed is not particularly limited. When coenzyme $Q_{10}$ containing reduced coenzyme $Q_{10}$ is used as coenzyme $Q_{10}$, an acidic condition of less than pH 7 is preferably employed by the addition of acid and the like, to protect from oxidation.

To obtain coenzyme $Q_{10}$ in the form of oil droplets in a poor solvent, a temperature not less than a temperature at which coenzyme $Q_{10}$ is melted, i.e., melting point of coenzyme $Q_{10}$ (about 48° C.), needs to be employed. To sufficiently melt coenzyme $Q_{10}$ to prevent presence of a solid component, a mixture of coenzyme $Q_{10}$ and a poor solvent is preferably stirred at 50° C.-80° C., more preferably 55° C.-60° C. Depending on the kind of the surfactant and organic solvent to be used, or when fats and oils which have low melting point and the like are co-present and the like, coenzyme $Q_{10}$ can be obtained in the form of oil droplets even at a temperature lower than the melting point of coenzyme $Q_{10}$. In this case, the temperature is not limited to the above-mentioned range and, for example, about 40° C. or above, more preferably about 45° C. or above, can be employed.

In the production method of the present invention, moreover, coenzyme $Q_{10}$ dispersed in the form of oil droplets in the above-mentioned poor solvent needs to be solidified at a temperature not higher than the melting point of coenzyme $Q_{10}$, while maintaining the shape of dispersion droplets. For solidification, the temperature only needs to be set to not more than the melting point of coenzyme $Q_{10}$. In view of the property of the obtained coenzyme $Q_{10}$ particles, the temperature is preferably cooled to 40° C. or below, further to 35° C. or below.

When the above-mentioned dispersion of coenzyme $Q_{10}$ is cooled at too high a cooling rate, the obtained coenzyme $Q_{10}$ particles have low uniformity, and the particle size becomes difficult to control. Therefore, the cooling rate is preferably not more than 1.2° C./min, more preferably not more than 1.0° C./min. To obtain coenzyme $Q_{10}$ particles more superior in the powder characteristics, not more than 0.5° C./min is particularly preferable, and not more than 0.2° C./min is most preferable. While the lower limit of the cooling rate is not particularly limited, when the cooling rate is extremely slow, problems of productivity occur such as frequent development of fine powder during formation of particles. Therefore, the cooling rate is preferably not less than 0.01° C./min, more preferably not less than 0.05° C./min.

In the production method of the present invention, melted coenzyme $Q_{10}$ needs to be dispersed in the form of oil droplets and cooled while maintaining the dispersion state. Thus, when coenzyme $Q_{10}$ is melted and dispersed in a poor solvent, stirring for cooling the dispersion is performed generally at required power per unit volume of not less than 0.01 kW/m³, preferably not less than 0.1 kW/m³, more preferably not less than 0.3 kW/m³, more preferably under flow conditions of not less than 0.5 kW/m³. While the upper limit of the required power for stirring is not particularly limited, when the required power is markedly high, bubbles from liquid free surface are severely sucked in, causing disorders when coenzyme $Q_{10}$ is solidified, such as deformation and the like. Thus, the upper limit of the required power for stirring is preferably not more than 1.5 kW/m³, more preferably not more than 1.0 kW/m³. The above-mentioned stirring is generally performed by rotation of impellers. As long as the above-mentioned flow is achieved, use of an impeller is not necessarily required and, for example, a method utilizing circulation of a liquid and the like can also be considered.

The thus-obtained coenzyme $Q_{10}$ solid particles are subjected to, for example, solid-liquid separation by centrifugation, filtration by pressurization, filtration under reduced pressure and the like, and further to cake washing as necessary, and a drying treatment by vacuum drying and the like to afford dry particles.

Since reduced coenzyme $Q_{10}$ easily gives oxidized coenzyme $Q_{10}$ as a by-product due to oxidation by molecular oxygen, when reduced coenzyme $Q_{10}$ or a mixture of reduced coenzyme $Q_{10}$ and oxidized coenzyme $Q_{10}$ is used as coenzyme $Q_{10}$ in the present invention, the series of operations are preferably performed in deoxygenated atmosphere. The deoxygenated atmosphere can be provided by purging with inert gas, reduced pressure, boiling or a combination thereof. Examples of the above-mentioned inert gas include nitrogen gas, helium gas, argon gas, hydrogen gas and carbon dioxide gas, with preference given to nitrogen gas.

According to the above-mentioned production method of the present invention, easily handlable coenzyme $Q_{10}$ particles can be obtained. The size of the obtained coenzyme $Q_{10}$ particles can be optionally changed according to the amount and kind the organic solvent or surfactant to be used, the above-mentioned stirring conditions for dispersing coenzyme $Q_{10}$ oily substance and the like.

Particularly, coenzyme $Q_{10}$ particles obtained by the preferable production method of the present invention are particles having high sphericity and superior in powder flowability characteristics. For example, when an aqueous solution containing an organic solvent is used as a poor solvent, coenzyme $Q_{10}$ particles having Dr. CARR's Flowability Index of not less than 80 can be obtained. From the aspect of powder flowability characteristics, a higher index is more preferable. By appropriately selecting the above-mentioned preferable production conditions, coenzyme $Q_{10}$ particles of not less than 85, further not less than 90, can also be obtained. When Dr. CARR's Flowability Index is less than 50, as in coenzyme $Q_{10}$ bulk powder obtained by a known crystallization method, problems occur in productivity and operability, since flowability is degraded, efficiency during delivery of coenzyme $Q_{10}$ particles decreases, an apparatus filling does not proceed smoothly and the like.

The Dr. CARR's Flowability Index is an index obtained by total evaluation of angle of repose, compressibility, angle of spatula and uniformity coef. of particles, which is defined in CHEMICAL ENGINEERING-Jan. 18, 1965. The definition relating to the aforementioned powder flowability index is shown in Table 1.

TABLE 1

| level of flowability | flowability index (total of points on right) | Angle of repose (°) | Point | Compressibility (%) | Point | Angle of spatula (°) | Point | Uniformity coef. (unit) | Point |
| --- | --- | --- | --- | --- | --- | --- | --- | --- | --- |
| Excellent | 90-100 | <25 | 25 | <5 | 25 | <25 | 25 | 1 | 25 |
|  |  | 26-29 | 24 | 6-9 | 23 | 26-30 | 24 | 2-4 | 23 |
|  |  | 30 | 22.5 | 10 | 22.5 | 31 | 22.5 | 5 | 22.5 |
| Good | 80-89 | 31 | 22 | 11 | 22 | 32 | 22 | 6 | 22 |
|  |  | 32-34 | 21 | 12-14 | 21 | 33-37 | 21 | 7 | 21 |

TABLE 1-continued

| level of flowability | flowability index (total of points on right) | Angle of repose (°) | Point | Compressibility (%) | Point | Angle of spatula (°) | Point | Uniformity coef. (unit) | Point |
|---|---|---|---|---|---|---|---|---|---|
| | | 35 | 20 | 15 | 20 | 38 | 20 | 8 | 20 |
| Fair | 70-79 | 36 | 19.5 | 16 | 19.5 | 39 | 19.5 | 9 | 19 |
| | | 37-39 | 18 | 17-19 | 18 | 40-44 | 18 | 10-11 | 18 |
| | | 40 | 17.5 | 20 | 17.5 | 45 | 17.5 | 12 | 17.5 |
| Passable | 60-69 | 41 | 17 | 21 | 17 | 46 | 17 | 13 | 17 |
| | | 42-44 | 16 | 22-24 | 16 | 47-59 | 16 | 15-16 | 16 |
| | | 45 | 15 | 25 | 15 | 60 | 15 | 17 | 15 |
| Poor | 40-59 | 46 | 14.5 | 26 | 14.5 | 61 | 14.5 | 18 | 14.5 |
| | | 47-54 | 12 | 27-30 | 12 | 62-74 | 12 | 19-21 | 12 |
| | | 55 | 10 | 31 | 10 | 75 | 10 | 22 | 10 |
| Very poor | 20-39 | 56 | 9.5 | 32 | 9.5 | 76 | 9.5 | 23 | 9.5 |
| | | 57-64 | 7 | 33-36 | 7 | 77-89 | 7 | 24-26 | 7 |
| | | 65 | 5 | 37 | 5 | 90 | 5 | 27 | 5 |
| Very, very poor | 0-19 | 66 | 4.5 | 38 | 4.5 | 91 | 4.5 | 28 | 4.5 |
| | | 67-89 | 2 | 39-45 | 2 | 92-99 | 2 | 29-35 | 2 |
| | | 90 | 0 | >45 | 0 | >99 | 0 | >35 | 0 |

The coenzyme $Q_{10}$ particles obtained by the preferable production method of the present invention have, for example, depending on the granulation conditions, an angle of repose of 20-45°. Particles having a smaller angle of repose are particles having superior flowability with roundness and free of corners.

The coenzyme $Q_{10}$ particles obtained by the production method of the present invention have high sphericity, which is, depending on the production conditions, for example, not less than 0.7, more preferably not less than 0.8.

The coenzyme $Q_{10}$ particles obtained by the preferable production method of the present invention have a spherical or granular shape. The mean particle size thereof is not particularly limited by stirring rate, cooling rate and the like during production, and can be appropriately adjusted. For easiness of handling, the mean particle size is generally not more than about 3 mm, further preferably not more than about 1 mm. In consideration of use in a mixture with other additives etc., it is particularly preferably not more than about 500 µm. more preferably not more than about 300 µm. On the other hand, since ultrafine particles are difficult to handle, the mean particle size of the obtained coenzyme $Q_{10}$ particles is generally adjusted to not less than about 1 µm. preferably not less than about 10 µm, more preferably not less than about 50 µm. That is, the mean particle size of the obtained coenzyme $Q_{10}$ particles is preferably 50-1000 µm. When used for tableting or as a soft capsule, the mean particle size is preferably 50-300 µm. When the mean particle size of coenzyme $Q_{10}$ particles exceeds 300 µm, problems occur since, for example, the filling amount during tableting and soft capsule filling is not uniform and the like.

In the production method of the present invention, excipient and coating agent are not required for granulation. Even when a surfactant or a water-soluble dispersing agent is used, since the amount is extremely small quantity, the obtained coenzyme $Q_{10}$ particles show a high coenzyme $Q_{10}$ content. For example, the particles have a coenzyme $Q_{10}$ content of not less than 90 wt %, more preferably not less than 95 wt %. When a surfactant or a water-soluble dispersing agent is not used, the obtained coenzyme $Q_{10}$ particles have a coenzyme $Q_{10}$ content of almost 100 wt %. Particles having a higher coenzyme $Q_{10}$ content are preferable, since production efficiency is improved, and the degree of freedom of design during formulation of preparations is high, when used for foods or pharmaceutical products. However, it does not exclude addition or mixing of coenzyme $Q_{10}$ particles obtained by the production method of the present invention to or with an excipient or coating thereof as necessary.

The coenzyme $Q_{10}$ in coenzyme $Q_{10}$ particles obtained by the preferable production method of the present invention has, for example, depending on the granulation conditions, crystallinity of not more than 90%, more preferably not more than 50%. When coenzyme $Q_{10}$ has low crystallinity, coenzyme $Q_{10}$ in the particles has a high ratio of amorphous structures. Consequently, the oral absorbability becomes higher as compared to coenzyme $Q_{10}$ bulk powder and coenzyme $Q_{10}$ processed product having a high crystallinity structure.

The coenzyme $Q_{10}$ particles obtained by the production method of the present invention can be tableted or filled in a soft capsule as they are, or can be processed in the same manner as with coenzyme $Q_{10}$ bulk powder, for example, dissolved in or mixed with fats and oils having affinity and the like, and put to use.

EXAMPLES

The present invention is explained in more detail in the following by referring to Examples. In Examples and Comparative Examples, the starting material of coenzyme $Q_{10}$ particles used was oxidized coenzyme $Q_{10}$ (bulk powder) or reduced coenzyme $Q_{10}$ (bulk powder) manufactured by Kaneka Corporation. The coenzyme $Q_{10}$ content of the particles used in the Examples was determined by the following HPLC analysis. The content of the obtained coenzyme $Q_{10}$ does not define the limit value of the content in the present invention.

(Hplc Analysis Conditions)
column: SYMMETRY C18 (manufactured by Waters) 250 nm (length) 4.6 mm (inner diameter),
mobile phase; $C_2H_5OH:CH_3OH=4:3(v:v)$,
detection wavelength; 210 nm,
flow rate; 1 ml/min,
retention time of reduced coenzyme $Q_{10}$; 9.1 min,
retention time of oxidized coenzyme $Q_{10}$; 13.3 min.

The crystallinity of coenzyme $Q_{10}$ in Examples was evaluated by the following X-RAY analysis apparatus (hereafter to be referred to as XRD).
(XRD Measurement Conditions)
apparatus: Geiger Flex RAD-rA manufactured by Rigaku,
X-ray used: Cu·Kα, X-ray intensity: 40 kV·100 mA, range:

2θ=2.7-140°, scanning rate: 2°/min, sampling intervals: 0.02°, divergence slit: 1°, receiving slit: 0.6 mm, scattering slit: 1°.

Example 1

Figure 1:
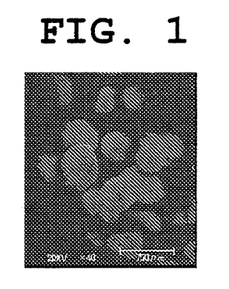
FIG. 1 is an SEM photograph of oxidized coenzyme $Q_{10}$ particles obtained in Example 1.

In a separable flask (inner volume 1000 mL) with a stirrer was charged 30 g of oxidized coenzyme $Q_{10}$ (bulk powder). Thereto was added 50 v/v % aqueous ethanol solution (600 mL) previously heated to 55° C., and the mixture was stirred at 400 rpm (required power for stirring per unit volume 0.34 kW/m$^3$) using a disc turbine blade (diameter 50 mm) while maintaining at 55° C. until oxidized coenzyme $Q_{10}$ was sufficiently melted and dispersed in the form of oil droplets. Thereafter, the dispersion was cooled to 35° C. at a cooling rate of 0.2° C./min under the same stirring conditions, and subjected to suction filtration and vacuum drying to give oxidized coenzyme $Q_{10}$ particles. The obtained particles had an oxidized coenzyme $Q_{10}$ content of 99.3 wt %. The obtained oxidized coenzyme $Q_{10}$ particles were observed under a microscope (digital microscope VH-6200, manufactured by KEYENCE, hereinafter the same) and found to be granular particles with a mean particle size of about 510 µm. In addition, the obtained oxidized coenzyme $Q_{10}$ particles were observed under a scanning electron microscope (S-800, manufactured by Hitachi, Ltd., hereinafter to be referred to as SEM). As a result, a particle shape having a smooth surface structure as shown in FIG. 1 was observed. The sphericity of the obtained coenzyme $Q_{10}$ particles was analyzed from the particle photograph taken by SEM and found to be 0.85. Furthermore, the obtained coenzyme $Q_{10}$ particles were evaluated by a powder tester (powder tester PT-R type, manufactured by Hosokawa Micron, hereinafter the same) for the powder flowability characteristics. As a result, the angle of repose was 40.4°, Dr. CARR's Flowability Index was 88.5 from other flowability characteristics, and the level of flowability characteristics was "Good". According to the crystallinity measurement by XRD, the crystallinity of the obtained coenzyme $Q_{10}$ particles was 42%.

Example 2

Figure 2:
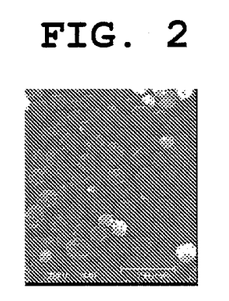
FIG. 2 is an SEM photograph of oxidized coenzyme $Q_{10}$ particles obtained in Example 2.

Using the same method and the same conditions as in Example 1 except that 30 v/v % aqueous ethanol solution containing 1 wt % gum arabic (600 mL) was used instead of 50 v/v % aqueous ethanol solution (600 mL), oxidized coenzyme $Q_{10}$ particles were obtained. The obtained particles had an oxidized coenzyme $Q_{10}$ content of 99.6 wt %. The obtained oxidized coenzyme $Q_{10}$ particles were observed under a microscope and found to be granular particles with a mean particle size of about 120 µm. In addition, the obtained oxidized coenzyme $Q_{10}$ particles were observed under SEM. As a result, a spherical particle shape having a smooth surface structure as shown in FIG. 2 was observed. The sphericity of the obtained oxidized coenzyme $Q_{10}$ particles was analyzed from the particle photograph taken by SEM and found to be 0.93. Furthermore, the obtained coenzyme $Q_{10}$ particles were evaluated by a powder tester for the powder flowability characteristics. As a result, the angle of repose was 32.9°, Dr. CARR's Flowability Index was 92.0 from other flowability characteristics, and the level of flowability characteristics was "Excellent". According to the crystallinity measurement by XRD, the crystallinity of the obtained coenzyme $Q_{10}$ particles was 32%.

Example 3

Using the same method and the same conditions as in Example 1 except that reduced coenzyme $Q_{10}$ (bulk powder, 30 g) and 40 v/v % aqueous ethanol solution (600 mL) were used and all operations were performed under a nitrogen atmosphere, reduced coenzyme $Q_{10}$ particles were obtained. The obtained particles had a reduced coenzyme $Q_{10}$ content of 99.4 wt %. The obtained reduced coenzyme $Q_{10}$ particles were observed under a microscope and found to be granular particles with a mean particle size of about 600 µm. In addition, the obtained reduced coenzyme $Q_{10}$ particles were evaluated by a powder tester for the powder flowability characteristics. As a result, the angle of repose was 33.9°, Dr. CARR's Flowability Index was 91.0 from other flowability characteristics, and the level of flowability characteristics was "Excellent".

Example 4

Using the same method and the same conditions as in Example 1 except that 50 v/v % aqueous acetone solution (600 mL) was used instead of 50 v/v % aqueous ethanol solution (600 mL), oxidized coenzyme $Q_{10}$ particles were obtained. The obtained particles had an oxidized coenzyme $Q_{10}$ content of 99.5 wt %. The obtained oxidized coenzyme $Q_{10}$ particles were observed under a microscope and found to be granular particles with a mean particle size of about 370 µm. In addition, the obtained oxidized coenzyme $Q_{10}$ particles were evaluated by a powder tester for the powder flowability characteristics. As a result, the angle of repose was 38.5°, Dr. CARR's Flowability Index was 87.5 from other flowability characteristics, and the level of flowability characteristics was "Good".

Comparative Example 1

Figure 3:
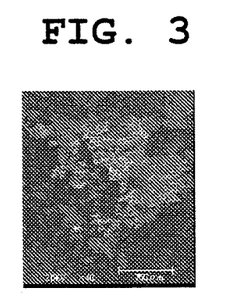
FIG. 3 is an SEM photograph of oxidized coenzyme $Q_{10}$ bulk powder of Comparative Example 1.

The oxidized coenzyme $Q_{10}$ bulk powder used as the starting material for Examples 1, 2 and 4 was observed under a microscope and found to have been dispersed as a finely divided powder with a mean particle size of about 40 µm. In addition, the oxidized coenzyme $Q_{10}$ bulk powder was observed under SEM and, as a result, a finely divided powder substance with low uniformity as shown in FIG. 3 was observed. Moreover, oxidized coenzyme $Q_{10}$ bulk powder was evaluated for the powder flowability characteristics by a powder tester. As a result, the angle of repose was 68.9°, Dr. CARR's Flowability Index was 41.0 from other flowability characteristics, and the level of flowability characteristics was "Poor".

Comparative Example 2

The reduced coenzyme $Q_{10}$ bulk powder used as the starting material for Example 3 was observed under a microscope and found to have been dispersed as a finely divided powder with a mean particle size of about 45 µm. In addition, the reduced coenzyme $Q_{10}$ bulk powder was evaluated for the powder flowability characteristics by a powder tester. As a result, the angle of repose was 57.7°, Dr. CARR's Flowability Index was 48 from other flowability characteristics, and the level of flowability characteristics was "Poor".

Comparative Example 3

Figure 4:
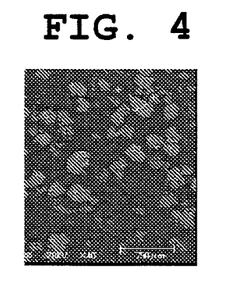
FIG. 4 is an SEM photograph of oxidized coenzyme $Q_{10}$ particles obtained in Comparative Example 3.

In a separable flask (inner volume 1000 mL) with a stirrer was charged 10 g of oxidized coenzyme $Q_{10}$ (bulk powder) and 99.5% ethanol (200 mL). Thereto was added Hi-Oleic safflower oil (3 mL) as an auxiliary solvent, and oxidized coenzyme $Q_{10}$ was completely dissolved in the mixed solvent thereof at 45° C. Thereafter, the mixture was cooled to 10° C.

at a cooling rate of 0.2° C./min while stirring at 150 rpm using a Maxblend blade to give a crystal. The oxidized coenzyme $Q_{10}$ particles obtained by suction filtration and vacuum drying had an oxidized coenzyme $Q_{10}$ content of 99.5 wt %. The obtained oxidized coenzyme $Q_{10}$ particles were observed under a microscope and found to be spherically-agglomerated crystals with a mean particle size of about 130 μm. In addition, the obtained oxidized coenzyme $Q_{10}$ particles were observed under SEM. As a result, an agglomerate of plate crystals as shown in FIG. 4 was observed. In addition, the obtained oxidized coenzyme $Q_{10}$ particles were evaluated by a powder tester for the powder flowability characteristics. As a result, the angle of repose was 43.7°, Dr. CARR's Flowability Index was 74.5 from other flowability characteristics, and the level of flowability characteristics was "Fair".

The evaluation results of the powder flowability characteristics of oxidized or reduced coenzyme $Q_{10}$ particles obtained in Examples 1-4 and oxidized or reduced coenzyme $Q_{10}$ bulk powders and oxidized coenzyme $Q_{10}$ particles obtained in Comparative Examples 1-3 are shown in Table 2.

TABLE 2

| item of measurement | Example 1 | | Example 2 | | Example 3 | | Example 4 | | Comp. Ex. 1 | | Comp. Ex. 2 | | Comp. Ex. 3 | |
|---|---|---|---|---|---|---|---|---|---|---|---|---|---|---|
| | Found | index | Found | index | Found | index | Found | index | Found | index | Found | index | Found | index |
| angle of repose (°) | 40.4 | 17.5 | 32.9 | 21 | 33.9 | 21 | 38.5 | 18 | 68.9 | 2.0 | 57.7 | 7.0 | 43.7 | 16 |
| compressibility (%) | 3.5 | 25 | 5.2 | 25 | 2.3 | 25 | 3.9 | 25 | 45.2 | 0.0 | 40.8 | 2.0 | 16.3 | 19.5 |
| angle of spatula (°) | 35 | 21 | 35.6 | 21 | 37.6 | 20 | 39 | 19.5 | 56.3 | 16 | 51.0 | 16 | 59 | 16 |
| uniformity coef. | 1.3 | 25 | 1.3 | 25 | 1.3 | 25 | 1.3 | 25 | 2.2 | 23 | 2.5 | 23 | 2.3 | 23 |
| total index | | 88.5 | | 92 | | 91 | | 87.5 | | 41 | | 48 | | 74.5 |
| level of flowability characteristics | | Good | | Excellent | | Excellent | | Good | | Poor | | Poor | | Passable |

The measurement results of mean particle size, coenzyme $Q_{10}$ content, sphericity and crystallinity of oxidized or reduced coenzyme $Q_{10}$ particles obtained in Examples 1-4 and oxidized coenzyme $Q_{10}$ particles obtained in Comparative Example 3 are shown in Table 3.

TABLE 3

| | Ex. 1 | Ex. 2 | Ex. 3 | Ex. 4 | Com. Ex. 3 |
|---|---|---|---|---|---|
| mean particle size (μm) | 510 | 120 | 600 | 370 | 130 |
| coenzyme $Q_{10}$ content (%) | 99.3 | 99.6 | 99.4 | 99.5 | 99.5 |
| sphericity | 0.85 | 1.93 | — | — | — |
| crystallinity (%) | 42 | 32 | — | — | — |

Example 5

Oxidized coenzyme $Q_{10}$ (60 g, bulk powder) and tetraglycerol monolaurate (0.4 g, manufactured by Sakamoto Yakuhin Kogyo Co., Ltd.: ML-310, HLB 10.3) were added to water (1000 g), and the mixture was gradually heated to 60° C. with stirring. After oxidized coenzyme $Q_{10}$ was completely melted, the mixture was cooled to 20° C. at a cooling rate of 1.0° C./min with stirring (required power for stirring 0.3 kW/m³). The obtained slurry was filtered, and the filtrated particles were washed with water and dried under reduced pressure to give oxidized coenzyme $Q_{10}$ particles. The obtained particles generally had a diameter of 100-300 μm, and showed good flowability and easy handling property.

Example 6

Reduced coenzyme $Q_{10}$ (60 g, bulk powder) and tetraglycerol monolaurate (0.4 g, manufactured by Sakamoto Yakuhin Kogyo Co., Ltd.: MO-3S, HLB 8.8) were added to water (1000 g), and the mixture was gradually heated to 60° C. with stirring. After reduced coenzyme $Q_{10}$ was completely melted, the mixture was cooled to 20° C. at a cooling rate of 1.0° C./min with stirring (required power for stirring 0.3 kW/m³). All the operations above were performed under a nitrogen atmosphere. The obtained slurry was filtered, and the filtrated particles were washed with water and dried under reduced pressure to give reduced coenzyme $Q_{10}$ particles. The obtained particles generally had a diameter of 100-300 μm, and showed good flowability and easy handling property.

Example 7

Reduced coenzyme $Q_{10}$ (60 g, bulk powder) and safflower oil (6 g) were mixed, and the mixture was heated to 60° C. and reduced coenzyme $Q_{10}$ was completely melted. This was added to water (1000 g) maintained at 60° C., which contained tetraglycerol monolaurate (0.4 g, manufactured by Sakamoto Yakuhin Kogyo Co., Ltd.: ML-500, HLB 13.5). The mixture was cooled to 20° C. at a cooling rate of 1.0° C./min with stirring (required power for stirring 0.3 kW/m³). All the operations above were performed under a nitrogen atmosphere. The obtained slurry was filtered, and the filtrated particles were washed with water and dried under reduced pressure to give reduced coenzyme $Q_{10}$ particles. The obtained particles generally had a diameter of 200-300 μm, and showed good flowability and easy handling property.

Example 8

Reduced coenzyme $Q_{10}$ (60 g, bulk powder) and sucrose laurate (0.4 g, manufactured by Mitsubishi Chemical Foods Co., Ltd.: Ryoto sugar ester L-1695, HLB 16) were added to water (1000 g), and the mixture was gradually heated to 60° C. with stirring. After reduced coenzyme $Q_{10}$ was completely melted, the mixture was cooled to 20° C. at a cooling rate of 1.0° C./min with stirring (required power for stirring 0.3 kW/m³). All the operations above were performed under a nitrogen atmosphere. The obtained slurry was filtered, and the filtrated particles were washed with water and dried under reduced pressure to give reduced coenzyme $Q_{10}$ particles. The obtained particles generally had a diameter of 100-300 μm, and showed good flowability and easy handling property.

Example 9

Oxidized coenzyme $Q_{10}$ (60 g, bulk powder), vitamin E (0.1 g) and hexaglycerol monolaurate (0.4 g, manufacby Sakamoto Yakuhin Kogyo Co., Ltd.: ML-500, HLB 13.5) were added to water (1000 g), and the mixture was gradually heated to 60° C. with stirring. After oxidized coenzyme $Q_{10}$ was completely melted, the mixture was cooled to 20° C. at a cooling rate of 1.0° C./min with stirring (required power for stirring 0.3 kW/m³). The obtained slurry was filtered, and the filtrated particles were washed with water and dried under reduced pressure to give oxidized coenzyme $Q_{10}$ particles. The obtained particles generally had a diameter of 50-300 µm, and showed good flowability and easy handling property.

Comparative Example 4

Oxidized coenzyme $Q_{10}$ (60 g, bulk powder) and sucrose stearate (0.4 g, manufactured by Mitsubishi Chemical Foods Co., Ltd.: Ryoto sugar ester S-570, HLB 5) were added to water (1000 g), and the mixture was gradually heated to 60° C. with stirring. After oxidized coenzyme $Q_{10}$ was completely melted, the mixture was cooled to 20° C. at a cooling rate of 1.0° C./min with stirring (required power for stirring 0.3 kW/m³). Oxidized coenzyme $Q_{10}$ mostly adhered to the walls of the container and solidified, and a part thereof formed a large mass with a diameter of about 2 cm.

Comparative Example 5

Reduced coenzyme $Q_{10}$ (60 g, bulk powder) and tetraglycerolpentaoleic acid ester (0.4 g, manufactured by Sakamoto Yakuhin Kogyo Co., Ltd.: PO-3S, HLB 3) were added to water (1000 g), and the mixture was gradually heated to 60° C. with stirring. After reduced coenzyme $Q_{10}$ was completely melted, the mixture was cooled to 20° C. at a cooling rate of 1.0° C./min with stirring (required power for stirring 0.3 kW/m³). All the operations above were performed under a nitrogen atmosphere. Reduced coenzyme $Q_{10}$ mostly adhered to the walls of the container and solidified, and a part thereof formed a large mass with a diameter of about 2 cm.

The invention claimed is:

1. A method of producing coenzyme $Q_{10}$ particles, comprising
   (a) mixing coenzyme $Q_{10}$ and a poor solvent by stirring at a temperature not less than the melting point of coenzyme $Q_{10}$, which results in dispersed coenzyme $Q_{10}$ in the form of oil droplets,
   (b) cooling the resulting dispersion to a solidification temperature of coenzyme $Q_{10}$ or below while stirring, thereby maintaining the dispersion to yield coenzyme $Q_{10}$ solid particles, and
   (c) performing solid-liquid separation to obtain dry coenzyme $Q_{10}$ particles,
   wherein the dry coenzyme $Q_{10}$ particles are spherical or granular particles having a mean particle size of 50 to 1000 µm, and
   wherein the poor solvent is an aqueous solution comprising an organic solvent and/or a high-HLB surfactant having an HLB of 6 or above wherein the concentration of the of the high-HLB surfactant in the poor solvent is not more than 1 wt %.

2. The production method of claim 1, wherein the poor solvent is an aqueous solution comprising at least one organic solvent selected from the group consisting of ketones, alcohols, nitriles and ethers.

3. The production method of claim 2, wherein the organic solvent is an alcohol having a carbon number of 1 to 5.

4. The production method of claim 2, wherein the poor solvent is an aqueous solution containing ethanol at a concentration of 10-70% by volume.

5. The production method of claim 1, wherein the high-HLB surfactant is at least one selected from the group consisting of partial glyceride of fatty acid, phospholipid, saponin, sucrose fatty acid ester, sorbitan fatty acid ester, sorbitan polyoxyethylene fatty acid ester, polyglycerin fatty acid ester and condensed ricinoleic acid polyglyceride.

6. The production method of claim 1, wherein the high-HLB surfactant is at least one selected from the group consisting of partial glyceride of fatty acid, sucrose fatty acid ester, sorbitan polyoxyethylene fatty acid ester and polyglycerin fatty acid ester.

7. The production method of claim 1, wherein the concentration of the high-HLB surfactant in the poor solvent is not less than 0.001 wt %.

8. The production method of claim 1, wherein the poor solvent further comprises a water-soluble dispersing agent.

9. The production method of claim 8, wherein the water-soluble dispersing agent is at least one selected from the group consisting of gum arabic, gelatin, agar, starch, pectin, carageenan, casein, alginic acids, soybean polysaccharides, pullulan, celluloses, xanthan gum, polyvinyl alcohol and a low-HLB surfactant having an HLB of less than 6.

10. The production method of claim 8, wherein the concentration of the water-soluble dispersing agent in the poor solvent is 0.001-5 wt %.

11. The production method of claim 1, wherein the dispersion of coenzyme $Q_{10}$ formed by step (a) of the method of claim 1 further comprises a material selected from the group consisting of fats, oils, waxes, fatty acids and fatty acid ester derivatives.

12. The production method of claim 1, wherein the stirring of the cooling step (b) of claim 1 is performed under the conditions of required power for stirring per unit volume of not less than 0.01 kW/m³.

13. The production method of claim 1, wherein the dispersion of coenzyme $Q_{10}$ is cooled at a cooling rate of 0.01-1.2° C./min.

14. The production method of claim 1, wherein the coenzyme $Q_{10}$ comprises reduced coenzyme $Q_{10}$.

15. The production method of claim 1, wherein the concentration of the high-HLB surfactant in the poor solvent is not more than 0.5 wt %.

16. A method of producing coenzyme $Q_{10}$ particles, comprising
   (a) mixing coenzyme $Q_{10}$ and a poor solvent by stirring at a temperature not less than the melting point of coenzyme $Q_{10}$, which results in dispersed coenzyme $Q_{10}$ in the form of oil droplets,
   (b) cooling the resulting dispersion to a solidification temperature of coenzyme $Q_{10}$ or below while stirring, thereby maintaining the dispersion to yield coenzyme $Q_{10}$ solid particles, and
   performing solid-liquid separation to obtain dry coenzyme $Q_{10}$ particles,
   wherein the dry coenzyme $Q_{10}$ particles are spherical or granular particles having a mean particle size of 50 to 1000 µm, and
   wherein the poor solvent is an aqueous solution comprising an organic solvent, and wherein the aqueous solution does not contain a high-HLB surfactant having an HLB of 6 or above.

17. The production method of claim 16, wherein the poor solvent is an aqueous solution containing ethanol at a concentration of 10-70% by volume.

* * * * *

UNITED STATES PATENT AND TRADEMARK OFFICE
CERTIFICATE OF CORRECTION

PATENT NO. : 8,568,779 B2
APPLICATION NO. : 12/522792
DATED : October 29, 2013
INVENTOR(S) : Kanaya et al.

Page 1 of 1

It is certified that error appears in the above-identified patent and that said Letters Patent is hereby corrected as shown below:

IN THE CLAIMS

Claim 1, column 21, lines 56-57, "concentration of the of the" should read:

"concentration of the"

Signed and Sealed this
Thirteenth Day of May, 2014

Michelle K. Lee
*Deputy Director of the United States Patent and Trademark Office*